United States Patent [19]

Feller et al.

[11] Patent Number: 4,816,446

[45] Date of Patent: Mar. 28, 1989

[54] HEPARIN DERIVATIVES

[75] Inventors: Wolfgang Feller, Melsungen; Rainer Störmer, Kassel; Annemarie Müller, Knüllwald-Niederbeisheim, all of Fed. Rep. of Germany

[73] Assignee: Intermedicat GmbH, Emmenbrucke, Switzerland

[21] Appl. No.: 744,198

[22] Filed: Jun. 13, 1985

[30] Foreign Application Priority Data

Jun. 16, 1984 [DE] Fed. Rep. of Germany ....... 3422518

[51] Int. Cl.$^4$ .................. A61K 31/725; C08B 37/10
[52] U.S. Cl. .................................. 514/56; 514/822; 536/21
[58] Field of Search ............... 536/21; 514/56, 822

[56] References Cited

U.S. PATENT DOCUMENTS 3,118,816  1/1964  Cushing ........................... 514/56
3,151,025  9/1964  Costello .......................... 514/56

FOREIGN PATENT DOCUMENTS 3403256  5/1985  Fed. Rep. of Germany .

Primary Examiner—John Rollins
Attorney, Agent, or Firm—Kenyon & Kenyon

[57] ABSTRACT

The invention comprises heparin derivative compounds which possess a low density lipoprotein lowering action without a significant anticoagulent effect, and are therefore useful in the treatment of disturbances of fat metabolism, especially hyperlipidemia. The heparin derivatives of the invention are derived from natural heparin, and are prepared by the hydrolysis of heparin and optionally, subsequent acylation at free amine groups of the hydrolyzed heparin.

21 Claims, 13 Drawing Sheets

Plasma/Acetate Buffer (1:1)

Heparin hydrolyzate according to Example 1

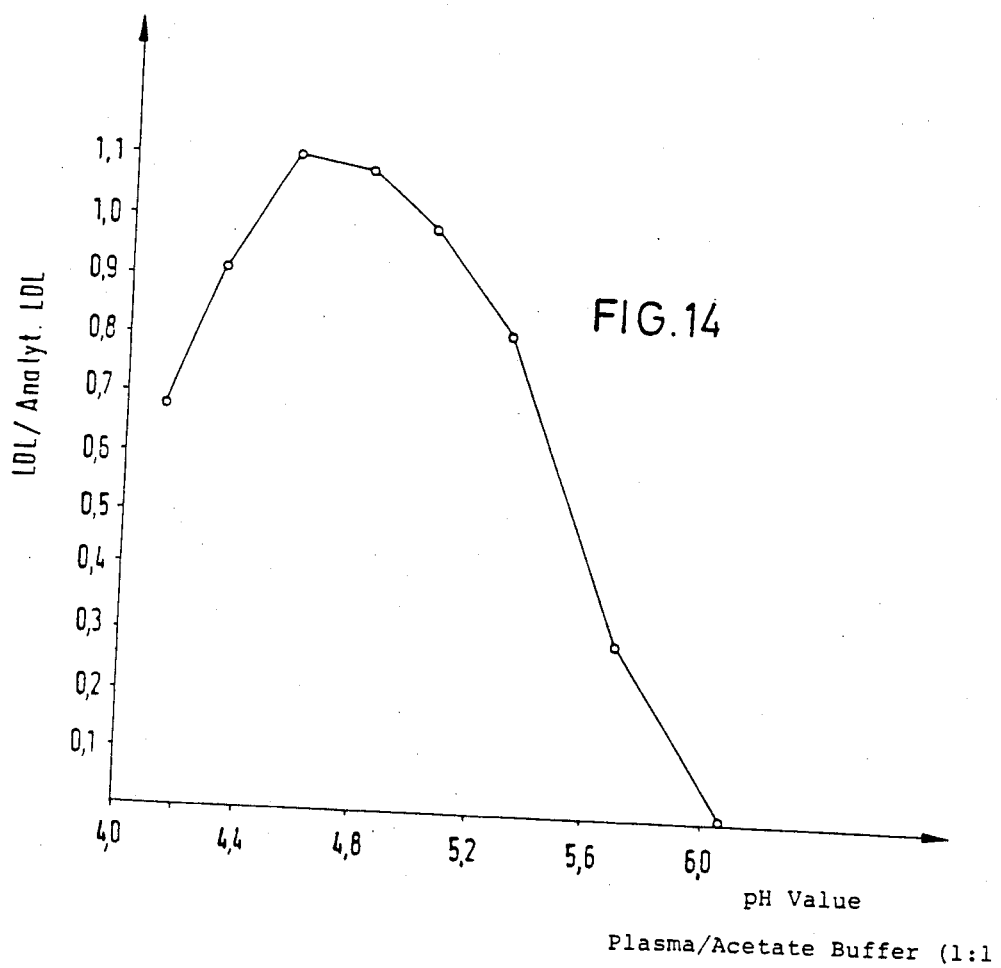

HEPARIN DERIVATIVES

BACKGROUND OF THE INVENTION

The present invention concerns heparin derivatives, processes for their preparation, pharmaceutical substances containing these heparin derivatives and their use in the treatment of disturbances in fat metabolism.

Sulfated glycosamino glycan heparin has long been in use a postoperative, subcutaneous thrombo-embollic prophylactic agent at low doses of $3 \times 5,000$ IU daily, but in relatively larger doses for the treatment of extracorporeal circulations for the prevention of blood coagulation when used in connection with, for example, blood oxygenation, surgery with the use of the heart-lung machine, hemodialysis, hemofiltration, hemoperfusion and plasmaphoresis. Even as part of the heparin therapy after thrombo-embolic conditions, i.e., venous thrombosis or pulmonary embolism, heparin salts are administered in intravenous doses of 30,000 to 40,000 IU/24 hours.

In such cases, heparin is known to have an inhibitory effect on the coagulation system by potentiating the action of the plasmatic inhibitor antithrombin III with regard to the coagulation factors Xa and thrombin. Independent of its influence on the coagulation system, it also acts in fat metabolism by induction of the release of the so-called clearing factor, a lipoprotein lipase bound to the vessels. The latter effect predestines heparin for the treatment of hyperlipidemia, for which it is administered preferably in low doses over a relatively long time.

A danger of hyperlipidemia is that in the plasma, lipids are not present in a free state but are conjugated with each other and with carrier proteins. Abnormal accumulation of lipoproteins (e.g., containing cholesterol), particularly low density lipoproteins, is associated with the development of atherosclerosis. See Robins and Angell, *Basic Pathology*, pages 271–74, 2nd Ed. (1976).

To decrease the associated effect of an increase in the coagulation time, which is dangerous for the patient, attempts were made to modify heparin chemically in such a way that, while still retaining its lipid-lowering action, it loses its anticoagulant potency which is expressed, for example, in its ability to inhibit coagulation in the blood plasma. Thus, the decoupling of lipid-lowering and coagulation-inhibiting action has been the subject of numerous publications. For example, the problem of whether low molecular weight heparin fractions or heparin fragments with a decreased anticoagulant action can be used therapeutically for the elevation of the lipoprotein lipase level is being studied intensively at present (K. Etienne et al., Br. J. Clin. Pharmac. 16: 712–714, 1983).

The chemical structure of heparin as well as some structural prerequisites for its action have been almost completely established. Thus it is known that the action of heparin on the fat metabolism is facilitated mainly by its O-sulfate groups (sulfuric acid ester groups) while the anticoagulant activity is correlated with the content of N-sulfate groups such as sulfamine groups. (K. Andrassy, "Nierenund Hochdruckkrankheiten," 10 (No. 3): 96, 1981). As is known by one skilled in the art, the anticoagulant effect as well as the effect of heparin on the so-called clearing factor declines during the course of acid hydrolysis of heparin with mineral acids, where the acid-labile, N-sulfate groups are cleaved more readily than the O-sulfate groups. Also known is the fact that both of the therapeutic effects of heparin discussed herein (mobilization of lipoprotein lipase and anticoagulant potency) are lowered or completely lost during the course of continued hydrolysis. For example, B. Casu et al. report in Arzneimittel -Forschung/Drug Res. 33(I): No. 1, 1983 a correlation between the fat-clearing activity and the behavior of $SO_3^-/COO^-$-groups in heparins and heparin sulfates.

U.S. Pat. No. 3,118,816 describes N-succinyl derivatives of heparin that can potentiate the activity of lipoprotein lipase in warm-blood animals without any apparent influence on the blood coagulation times. Such derivatives are prepared by refluxing heparin with aqueous 0.09 N HCl and then reacting with succinyl chloride to form N-succinyl heparin, in which between 25% and 35% of the glucosamine-N-atoms have been succinylated. The product has a coagulation activity of 7 USP units/mg.

A considerably more drastic hydrolysis method for heparin is disclosed in German Offenlegensschrift DE-OS No. 31 23 806, wherein heparins of different origins are subjected to a hydrolysis with 0.33N mineral acids, e.g. hydrochloric acid, at 100° for 6 hours, which hydrolyze the acid-labile sulfamine groups completely and the acid-stable O-sulfate groups partially. A subsequent succinylation with succinic anhydride results in a product with a coagulation activity below 0.05 USP units/mg.

Because of the extremely drastic hydrolysis conditions or due to the conditions of the derivation reaction, the polyanionic structural characteristics of the succinylated heparin derivatives contribute to an increase in the lipid-lowering effect in contrast to pure, underivatized hydrolyzates, but only about half of the lipid-lowering activity of the heparin used in the reaction is obtained. Moreover, the foregoing studies, without exception, have as their objective the indirect therapeutic lowering of the lipid level in the blood by the use of the modified heparins, i.e. by elevation of the enzyme activity of a lipoprotein lipase (clearing factor).

German Offenlegensschrift DE-OS No. 31 35 814 discloses the selective precipitation of low-density lipoproteins (LDL) or beta-lipoproteins from whole serum or plasma with the aid of heparin at acid pH values with the consequent direct and specific reduction of the content of this risk factor in the blood. The disadvantage of this method, however, is the lasting risk to the patient due to the strong anticoagulant effect induced by the relatively high heparin level required for the therapeutic treatment.

Thus, there remains a need for a heparin derivative that causes the precipitation of low-density lipoproteins while minimizing or eliminating the anticoagulent effect thereof.

SUMMARY OF THE INVENTION

It is an object of the invention to provide heparin derivatives for the treatment of hyperlipidemia and other diseases and afflictions characterized by an excess of lipids or lipid derivatives in a subject.

It is another object of this invention to provide heparin derivatives that cause the precipitation of low density lipoproteins (LDL) while minimizing the anticoagulent effect thereof.

These and other objects are achieved through the provision of heparin derivatives which specifically precipitate LDL in vitro and in vivo in the acid pH range. This is achieved without any significant influence on blood coagulation and without necessitating the succinylation of the hydrolyzates, which is required when heparin interacts with the clearing factor.

Thus, the invention comprises a heparin derivative compound characterized by a low density lipoprotein lowering action while minimizing or eliminating an anticoagulent effect normally associated with heparin. More specifically, the invention comprises a heparin derivative compound selected from the group consisting of hydrolyzed heparin and acylated hydrolyzed heparin which is characterized by its low density lipoprotein lowering action without a significant anticoagulent effect; said heparin derivative compound is further characterized by a coagulation activity of about 20 IU/mg or less and low binding affinity to antithrombin III as compared to heparin.

The invention also includes a process for the preparation of low density lipoprotein-precipitating heparin derivatives from natural heparin which comprises subjecting heparin and/or any desired salts thereof to a mild, controlled, acid hydrolysis reaction at a predetermined acid pH for a predetermined period of time; cooling the reaction and ajusting the pH to a level higher than the predetermined acid pH by the addition of an alkali to create a reaction product; dialyzing the reaction product; and drying the reaction product. The process may further comprise acylating the reaction product at free amine groups thereof to form a hydrolyzed, acylated heparin derivation capable of precipitating low density lipoproteins with little or no anticoagulent effect.

The invention contemplates a pharmaceutical preparation for the treatment of hyperlipidemia and the prevention of angionesis of tumors comprising a heparin derivative selected from the group consisting of hydrolyzed heparin and hydrolyzed heparin that has been acylated at free amine groups. The invention further contemplates a method of treatment for hyperlipidemia as well as a method of treatment for the prevention of angionesis of tumors which comprises administering to a volume of blood, plasma or solutions thereof a therapeutically effective amount of a heparin derivative selected from the group consisting of hydrolyzed heparin and hydrolyzed heparin acylated at free amine groups.

The heparin derivatives of the invention exhibit, in comparison with generally employed heparins (coagulation activity: 140–180 IU/mg), little, if any, anticoagulent effect while being capable of causing the precipitation of low-density lipoproteins in the acid pH range. The simultaneous elimination of other lipoproteins from the plasma, such as high density lipoproteins, is minimized or prevented.

BRIEF DESCRIPTION OF THE DRAWINGS

FIG. 14 demonstrates the pH dependence of the LDL precipitation employing a succinylated heparin hydrolyzate prepared according to process of the invention.

DETAILED DESCRIPTION OF THE INVENTION

Figure 1:
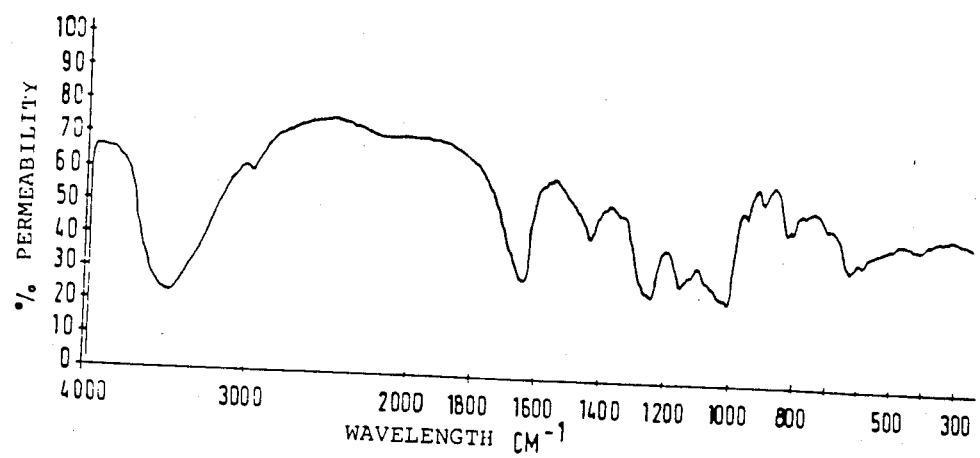
FIG. 1 shows the IR spectrum of the heparin hydrolyzate according to the invention (KBr pellet)

The heparin derivatives of the invention provide for the treatment of hyperlipidemia and other diseases and afflictions characterized by an excess of lipids in the blood, while minimizing or eliminating the anticoagulant effect of these heparin derivatives.

The heparin derivatives of the invention selectively act to precipitate low density lipoproteins (LDL) from the blood, thereby reducing the risk of a high plasma concentration of them in the blood and the associated development of atherosclerosis. The heparin derivatives of the invention are basically of two types: heparin derivatives prepared by hydrolysis of heparin, and heparin derivatives prepared from heparins by hydrolysis and subsequently acylated at free amine groups.

In general, the heparin derivatives of the invention prepared by the hydrolysis of heparin are generally characterized by the following parameters:

(a) Appearance: white, amorphous, slightly hygroscopic substance;

(b) Content of free amine groups: 50 to 400 $\mu$mol/g.

(c) Ratio of uronic acid to hexosamine content: 0.97–0.995.

(d) Specific rotation: $(\alpha)_D^{20} = +35°$ to $60°$.

(e) Coagulation activity: 1.0 to 20 IU/mg.

(f) Metachromatic dye effect in comparison with heparin (=1.0): 0.10 to 0.90 (measured with toluidine blue).

(g) Mean molecular weight: 2,000 to 30,000 D.

(h) Suitability as substrate for heparinase (EC 4.2.2.7) from Flavobacterium heparinum: reaction rate at substrate saturation (at 30° C. and pH 7.0), relative to that of the heparin used for the preparation (=100%): 10% to 100%.

(i) Binding to antithrombin III (AT III): An affinity chromatography separation over human antithrombin III bound to Sepharose ® does not reveal any portion with high binding affinity (high-affinity heparin) in comparison with the heparin used for the preparation, whereas the portion with low affinity (low-affinity heparin) is always lower than in the heparin used for the preparation.

(k) IR-Spectrum: Increase in the intensity of the bands at 1130 to 1160 cm$^{-1}$ in comparison with the heparin used for the preparation.

(l) $^{13}$C-NMR-Spectrum: Reduction in the intensity of the signals at 97.8 and 58.7 ppm. Increase in the intensity of the two pH-dependent signals at 92.1 to 97.8 ppm and 55 to 56 ppm in comparison with heparin.

(m) $^1$H-NMR-Spectrum (400 MHz): Reduction in the intensity of the signal at 3.25 ppm (A-2s) in comparison with the signal at 3.40 ppm (A-2s) for heparin.

The heparin derivatives according to the invention prepared from natural heparins by hydrolysis and subsequent acylation at free amine groups are generally characterized by the following parameters:

(a) Appearance: white, slightly hygroscopic substance.

(b) Content of free amino groups: 2 to 10 μmol/g.

(c) Ratio of uronic acid and hexosamine content: 0.97 to 0.995.

(d) Specific rotation: $(\alpha)_D^{20} = +30°$ to $60°$.

(e) Coagulation activity: 10-20 IU/mg.

(f) Metachromatic dye effect in comparison with heparin (=1.0): 0.10 to 0.90 (measured with toluidine blue).

(g) Mean molecular weight: 2,000 to 30,000 D.

(h) Suitability as substrate for heparinase (EC 4.2.2.7) from Flavobacterium heparinum: reaction rate at substrate saturation (at 30° C. and pH 7.0), relative to the heparin used for the preparation (=100%): 10% to 100%.

(i) Binding to antithrombin III (AT III): An affinity chromatography separation over human antithrombin III bound to Sepharose ® does not reveal any portion with high binding affinity (high-affinity heparin) whereas the portion with low affinity (low-affinity heparin) is always lower than in the heparin used for the preparation.

(k) $^1$H-NMR-Spectrum (400 MHz): approximately identically strong signals at 3.25 and 3.40 ppm in the case of acetylation.

Heparins of the most dissimilar provenance may be the starting point of the heparin derivatives prepared by hydrolysis. For example, commercial heparins from bovine lungs, pig, sheep or bovine mucosa may be used. Alkali salts or salts of alkaline earth metals, e.g., sodium salts or calcium salts of heparins, or salts with organic cations can be used for the preparation of the heparin derivatives according to the invention.

There are no restrictions with regard to the molecular weights of the heparins or heparin salts that are used. Heparin or heparin salts can be used for the preparation of the heparin derivatives that have molecular weights in the range between about 2,0000 and 30,000D, but smaller, partial fractions with mean molecular weights that fall within the mentioned range can also be used. Preferred for use are heparins with a mean molecular weight in the range of about 11,000 to 17,000D.

The heparin derivatives of the invention may be prepared, in a preferred embodiment, by subjecting natural heparin and/or its salts to a mild, controlled acid hydrolysis with aqueous 0.2 to 0.33M acid at 45 to 70° C. and a pH in the range from about 1.0 to 5.0 for 90 minutes to 30 hours, followed by an interruption of the reaction by cooling to about 30° C. or below and adjusting the pH to between about 6.0 and 8.0 by the addition of an alkali. The reaction product is then dialyzed or diafiltered against water and isolated from aqueous solution by known methods. If needed, free amine groups of the resulting compounds may then be acylated by known methods.

Fragments prepared by cleavage reactions such as deamination with HNO$_2$ or fractions prepared by known separation and fractionation methods such as alcohol precipitation or separation according to the molecular weight or the charge density can be used as starting materials for the hydrolysis step. The use of heparin preparations with a purity below the purity of the preparation intended for injections can also be used in the hydrolysis step. Preferred for use are partial fractions of heparin and its alkali salts or salts of alkaline earth metals with a mean molecular weight between 11,000 and 17,000D.

Mineral acids may be used for the preparation of the heparin derivatives according to the invention which surprisingly exhibit a reduced anticoagulant activity while retaining their LDL-lowering effect intact. The use of hydrochloric acid is preferable as the mineral acid, but other acids that can produce an acid pH adequate for the hydrolysis are also suitable. An acid buffer with a pH of about 1.0 can be added to the reaction mixture.

The heparin derivatives according to the invention may also be prepared by using a cation exchanger in the H$^+$—form as an acid source. Commercial exchange resins can be used as exchangers; an example is the ion exchange resin Dowex ®50 W×8.

The hydrolysis must be carried out under very mild conditions and within relatively narrow limits regarding temperature, reaction time and pH to prevent a complete hydrolysis of the sulfamine groups of heparin, as observed in the process according to German Offenlegensscrift DE-OS No. 31 23 806. Mineral acids, preferably hydrochloric acid, are used in amounts that result in an acid concentration between about 0.2 and 0.33M in the reaction solution. At reaction temperatures between 60 to 70° C., the reaction time is less than 90 minutes, and preferably 60 to 80 minutes, with a lower acid concentration increasing the hydrolysis time. Longer hydrolysis times are also needed at constant acid concentration and a lower reaction temperature below 50° C. to obtain the same degree of hydrolysis and the consequent above-mentioned characteristics of the products. Thus, the process parameters of temperature, pH and hydrolysis time are mutually dependent.

After a maximal hydrolysis time of 90 minutes at 70° C., the reaction is interrupted by cooling to between 30° and 0° C. and adjusting the pH to between about 6.0 and 8.0. Cooling can be accomplished by immersion in an ice bath, by thermostatic control or some other known cooling method.

Normally, the pH is adjusted by adding an aqueous solution of alkali metal hydroxide in an amount adequate to furnish the exact context of hydroxide ions needed for the neutralization of the mineral acid in the solution.

The reaction product is then dialyzed against distilled, pyrogen-free water or diafiltered through ultrafiltration membranes and isolated by known methods.

This isolation process may consist, for example, of spray-drying or lyophilizing the solution. Alternatively, the reaction products can also be isolated by precipitating them from their solutions with three to six times the volume of alcohol, preferably methanol or ethanol, or with an equal volume of acetone, and the precipitates are then dried by known methods.

A white, amorphous, slightly hygroscopic powder is obtained in good yield by these processes. The heparin derivatives according to the invention obtained by these methods have an anticoagulant activity in the range of from about 1.0 to 20 IU/mg.

The course of the reaction, i.e., the progress of the hydrolysis at the N-sulfate and O-sulfate groups, can be followed by measuring, for example, the coagulation activity. For this purpose, samples are removed from the reaction mixture during the reaction, buffered in the neutral range, diluted with saline solution and added to a sample of human plasma. The activated, partial thromboplastin time (apTT) is then determined in this mixture with a commercially available test kit, e.g. Pathromtin ® furnished by Behringwerke, Marburg. Another suitable method for monitoring the course of the hydrolysis reaction is by measuring the metachromia by mixing a sample of the reaction solution with basic dyes such as azure-A or toluidine blue. This test utilizes the characteristic of heparin to form compounds stained during the complexing with basic dyes of the above mentioned type, which decreases as the hydrolysis progresses.

The heparin derivatives obtained by the processes according to the invention can be chemically characterized, being different from the starting heparin as well as from the products obtained according to German Offenlegensschrift DE-OS No. 31 23 806 and U.S. Pat. No. 3,118,816. Thus, the heparin derivatives of the invention generally demonstrate an obtained content of free amine groups of from about 50 to 400 $\mu$mol/g, preferably from 60 to 200 $\mu$mol/g, a specific rotation $(\alpha)_D^{20}$ in the range of about $+35$ to $+60°$, preferably from $+40°$ to $+55°$, a coagulation activity in the range from about 1.0 to 20.0 IU/mg, preferably 1 to 10 IU/mg, weak binding to antithrombin III, a metachromatic dye effect preferably in the range of about 0.60 to 0.90 (in comparison to heparin, which is set equal to 1.0 of 0.10 to 0.90), a reaction rate in enzyme reactions with heparinase (E.C. 4.2.2.7) from Flavobacterium heparinum (relative to heparin, which is set equal to 100%) of about 10 to 100%, preferably 45 to 70%, and a mean molecular weight in the range from about 2,000D to 30,000D, preferably in the range of 11,000D to 17,000D.

Figure 2:
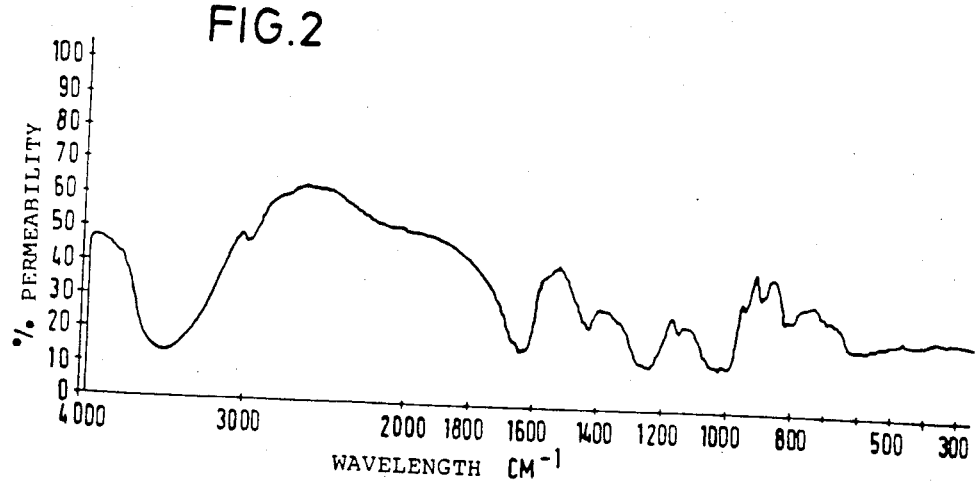
FIG. 2 shows the IR spectrum of the heparin used for the preparation of the heparin hydrolyzate according to the invention (KBr pellet)
Figure 3:
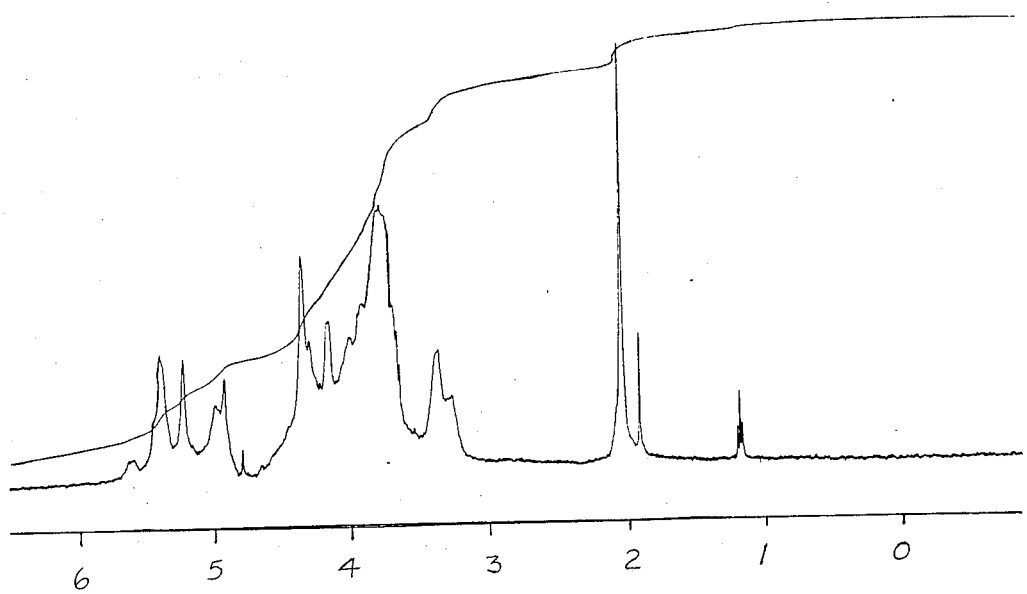
FIG. 3 shows the 400 MHz $^1$H-NMR spectrum of the heparin hydrolyzate according to the invention.
Figure 4:
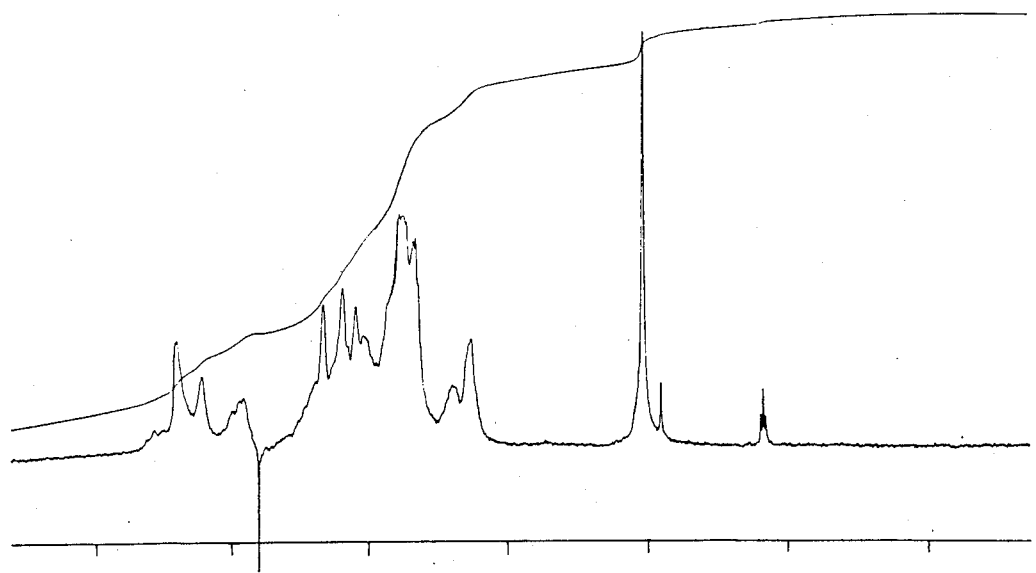
FIG. 4 shows the 400 MHz $^1$H-NMR spectrum of the heparin used for the preparation of the heparin hydrolyzate according to the invention.
Figure 5:
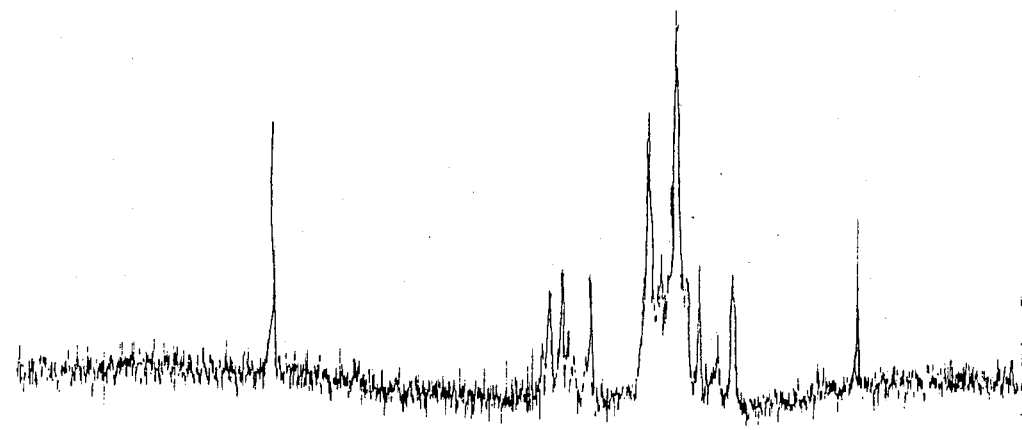
FIG. 5 illustrates the $^{13}$C-NMR spectrum of the heparin hydrolyzate according to the invention.
Figure 6:
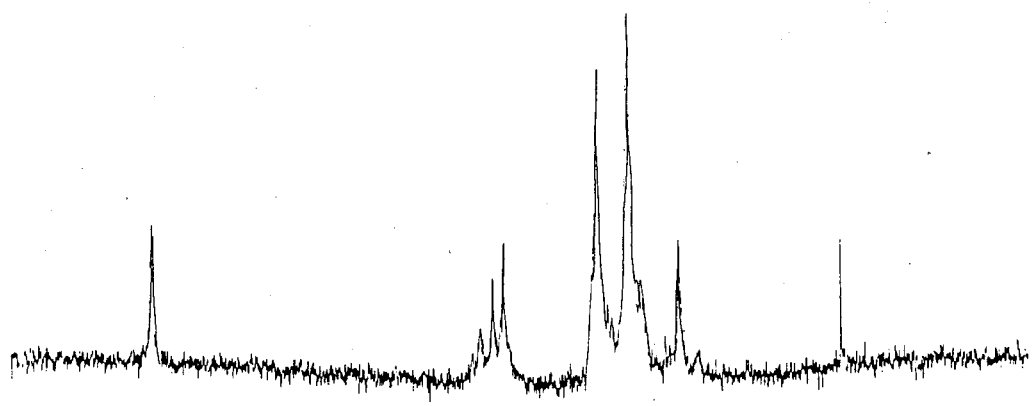
FIG. 6 illustrates the $^{13}$C-NMR spectrum of the heparin used for the preparation of the heparin hydrolyzate according to the invention.

The spectra of FIGS. 1 through 6 may be used to differentiate the heparin derivatives according to the invention from natural heparins. More specifically, FIGS. 1 and 2 show the IR spectra of the heprin hydrolyzate according to the invention and the heparin used for its preparation (KBr pellet). FIGS. 3 and 4 show the 400 MHz $^1$H-NMR spectra of the heparin hydrolyzate according to the invention and the heparin used for its preparation (50 mg/ml D$_2$O; internal standard: HDO; $\delta=4.8$ ppm rel. TMS) and FIGS. 5 and 6 illustrate the $^{13}$C-NMR spectra of the heprin hydrolyzate according to the invention and the heparin used for its preparation (200 mg/ml D$_2$O; internal standard: trimethylsilyl propionate; measuring frequency: 22.628 MHz).

The $^{13}$C-NMR-spectra of the heparin derivatives of the invention show that the cleavage of sulfate groups from the 2-deoxy-2-sulfamido-$\delta$-D-glucopyranosyl-6-sulfate occurs under the hydrolysis conditions according to the invention. The $^{13}$C-NMR-spectra of the glucosamine-C$_2$-group (A-2s and A-2a) are similar to those of heparin sulfate (B. Casu et al., Arzneimittel-Forschung/Drug Res. 33 (I): No. 1, 135–142, 1983).

Additional details of the chemical structure of the heparin derivatives of the invention can also be obtained from the $^{13}$C-NMR-spectra. For example, the percentage of N-sulfate groups (sulfamide) can be calculated from the signal intensity ratio of the C$_2$-signals A-2s and A-2a (B. Casu et al., loc. cit). Thus, while a percentage content of $\geq 86\%$ N-sulfate is normally found for heparins, this percentage is between 40 and 90% in the heparin derivatives according to the invention. This range was obtained by graphic evaluation of the intensity of the A-2s and A-2a signals.

Together with suitable excipients and adjuvants, heparin derivatives according to the invention can be formulated into pharmaceutical products that can be used for the treatment of hyperlipidemia. For this purose, they can be mixed in vivo or in vitro with human plasma at pH levels below about 6.0, and they are then capable of precipitating specifically the low-density lipoprotein (LDL) that is known as a risk factor in the development of arteriosclerosis and remove it in this manner from the plasma. Consequently, the heparin derivatives according to the invention can then be utilized instead of natural heparin or its salts for therapy and diagnosis without the danger of a significant anticoagulant effect or hemorrhage.

The surprisingly high specificity with which the heparin derivatives according to the invention act as precipitating agents for LDL makes them particularly suitable for the treatment of hyperlipidemia. This special suitability also results from the fact that the conditions of the heparin hydrolysis according to the present invention can be adapted to the conditions of the LDL precipitation, whereby undesirable competing reactions, depolymerization or nonspecific reactions leading to yellow colored hydrolysis products, which have been observed repeatedly in the art, can be eliminated.

The heparin hydrolyzates according to the invention, which may have a proportion of free amine groups in the molecule that rises to a level 10 to 20 times greater than that of the starting heparin depending on the duration of the hydrolysis reaction, may also be substituted at the free amine groups by known methods. Consequently, derivatives may be obtained by reaction of the heparin hydrolyzates, e.g., with anhydrides or acid halides of oxalic acid, malonic acid, succinic acid, haloacetic acid, halopropionic acid, haloacrylic acid or, if needed, substituted phthalic acid, in which the free amine groups are substituted up to a maximum of 400 umol/g with residues containing a terminal carboxyl group. Furthermore, the free amine groups produced by the hydrolysis step can also be reacted with acid halides or acid anhydrides of formic acid, acetic acid, propionic acid or butyric acid, for example.

An additional variant of the process of the invention consists of initially increasing the content of the O-sulfate groups of heparin and then subjecting this product in a second step to the described acid hydrolysis. The introduction of the O-sulfate groups (sulfate ester) can be carried out, for example, according to the process described by C. R. Ricketts, Biochemical Journal 51: 129–133, 1952, or O. Larm et al., Carbohydrate Research 73: 332,336, 1979.

The heparin derivatives according to the invention may be used as pharmaceutical substances in the form of their aqueous solutions by the addition of conventional preservatives such as benzyl alcohol, adjusted to a pH in the range from 5.0 to 8.0 and appropriate correction of the osmolarity. Such pharmaceutical substances can be stored for years in the form of sterile, aqueous solutions by the addition of known solvents and stabilizers, or as solids. The heparin derivatives may be also combined with other known active substances. Moreover, they can be sterilized by the use of known methods such as sterile filtration or steam or heat sterilization, e.g., at 105° C. for 30 minutes.

The heparin derivatives can be administered in solution form, especially intravenously, because of their low anticoagulant activity and low toxicity. Since they retain their ability to precipitate LDL in the acid pH range, like heparin, their preferred application lies in the treatment of blood or plasma in extracorporeal circulations or in regular stored blood or plasma, in the treatment of disturbances of the lipid metabolism by the precipitation of LDL, which is described analogously in German Offenlegensschrift DE-OS No. 31 35 814 for the precipitation of LDL with heparin.

Other indicated areas of application for the heparin derivatives according to the invention is the prevention of the angionesis of tumors, as described for heparin by J. Folkmann in Science 221: 719, 1983.

The invention is explained in more detail by the following examples.

EXAMPLE 1

Thirty grams of heparin with a mean molecular weight of 15,000D was dissolved in 480 ml of distilled, pyrogen-free $H_2O$ and mixed with 240 ml of 1N hydrochloric acid in a reaction vessel preheated to 70° C. The reaction mixture was maintained at 70° C., The pH was 1.0. After a hydrolysis period of 80 minutes, the reaction was interrupted by cooling in an ice bath and the pH of the reaction mixture was adjusted to between 6.8 and 7 by the addition of 30 ml of 5N sodium hydroxide solution. The reaction product was dialyzed against distilled, pyrogen-free water and spray-dried. 25 grams of a white, hygroscopic product with a coagulation activity of 1.9 IU/mg was obtained, the activity of which was tested according to the US-Pharmacopoeia XX and expressed in international units. The third international heparin standard was used as the standard of comparison.

The uronic acid content in the product was determined according to T. Bitter et al., Analytical Biochem. 4: 330, 1962, and glucuronolactone was used as standard. The product had a uronic acid content of 28.2%. The content of hexosamine groups was determined colorimetrically according to R. E. Hurst, et al., Analytical Biochem. 15: 88, 1981. The ratio or uronic acid to hexosamino group content was 0.98.

The content of N-amine groups in the product was determined with 2,4,6-trinitrobenzene-1-sulfonic acid according to K. Satake et al., J. Biochem. 47: 654, 1960, and glycine was always used as a comparison substance. While the content of free amine groups in commerical heparins is in the range of about 10 to 50 $\mu$mol/g, the product of Example 1 had a value of 129 $\mu$mol/g.

The metachromatic dye effect, i.e., the property of heparin and its derivatives in triggering metachromatic changes in the UV/VIS-spectrum of basic dyes (e.g. toluidine blue), was tested according to Silbert, Biochem. Biophys. Res. Commun. 69: 570, 1976, with heparin and the product. While the greatest metachromatic effect could be measured with heparin, the hydrolyzate showed a distinctly weaker effect. The slopes of the two linear curves (metachromatic effect as function of concentration) were to one another as 1 (heparin) : 0.65.

The rate of reaction of heparinase (E.C. 4.2.2.7) from Flavobacterium heparinum with heparin and its derivatives as substrate depends to a large degree on the structure of the respective substrate. Conversely, therefore, the degree of structural deviation of the substrate from heparin can be expressed as the ratio of the heparinase activity of heparin to the activity of the tested derivative. The activity was measured under the following conditions according to A. Linker, Methods in Enzymology 28: 1972, and PCT Patent/US No. 81/01081: Heparinase was isolated from Flavobacterium heparinum by chromatography on hydroxyl apatite and phosphocellulose. Samples of heparin and heparin derivative in the respective amount of 20 $\mu$l (25 mg/ml) and 20 $\mu$l heparinase solution were mixed with 2.5 ml of a buffer mixture of 0.25M sodium acetate solution and 0.025M calcium acetate solution (pH 7.0). The enzymatic reaction was recorded at 30° C. by registering the changes in extinction at 232 nm as a function of time. The slope of the time/conversion curve of heparin was set equal to 100%. Preliminary trials were performed to ascertain that the reaction occurred at substrate saturation. A rate of reaction of 54%, relative to heparin, was found for the product from Example 1.

The specific rotation of the starting heparin had a mean of +50.9°; a specific rotation $(\alpha)_D^{20}$ of +42.5° was found for the product from Example 1.

The molecular weight or the molecular weight distribution of the hydrolyzate according to Example 1 did not change in comparison with the heparin used as a starting material. A mean molecular weight of 15,000 was determined.

Figure 7:
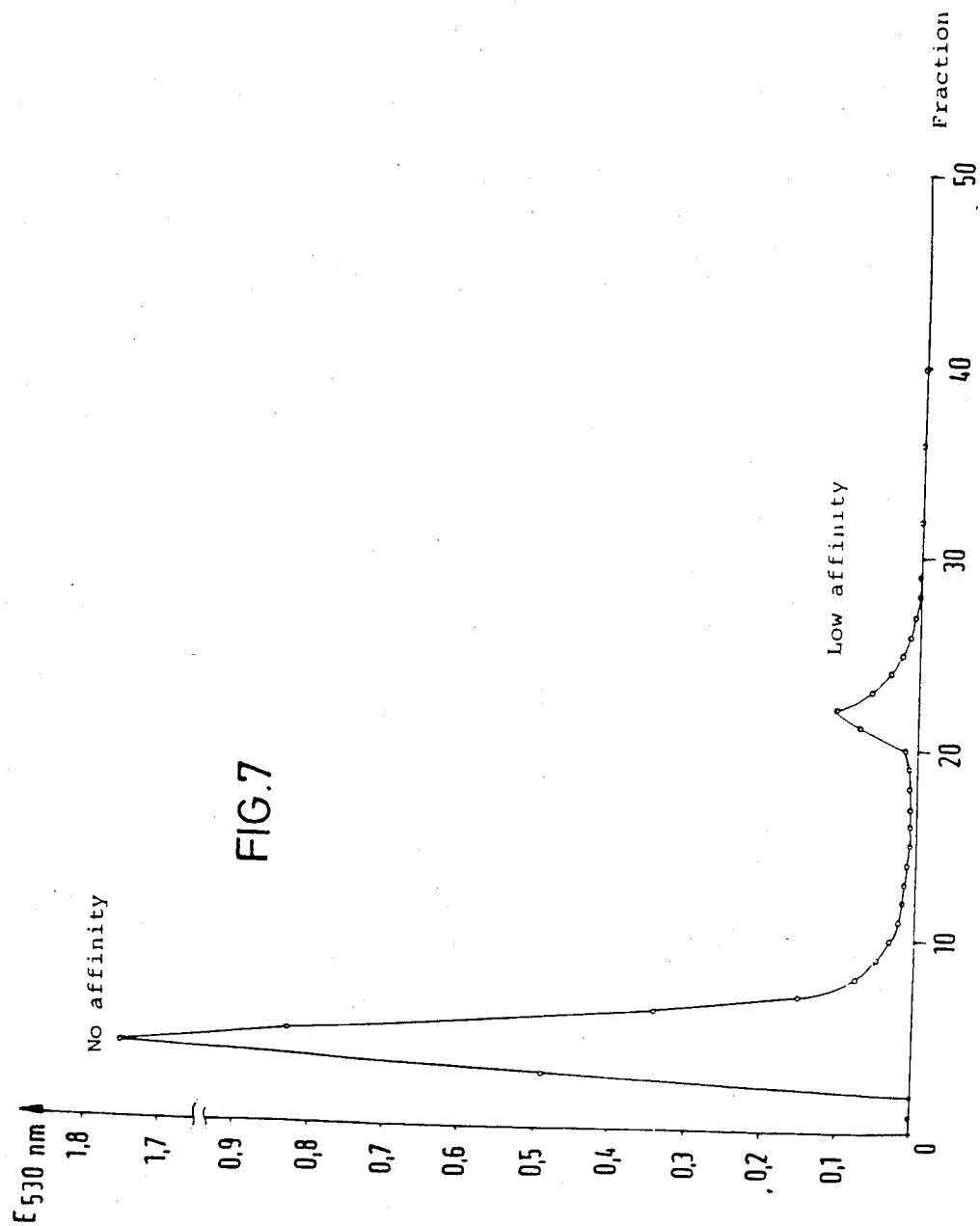
FIG. 7 illustrates the elution profile of the affinity chromatography of the heparin hydrolyzate according to the invention on antithrombin III coupled to Sepharose ®4B.
Figure 8:
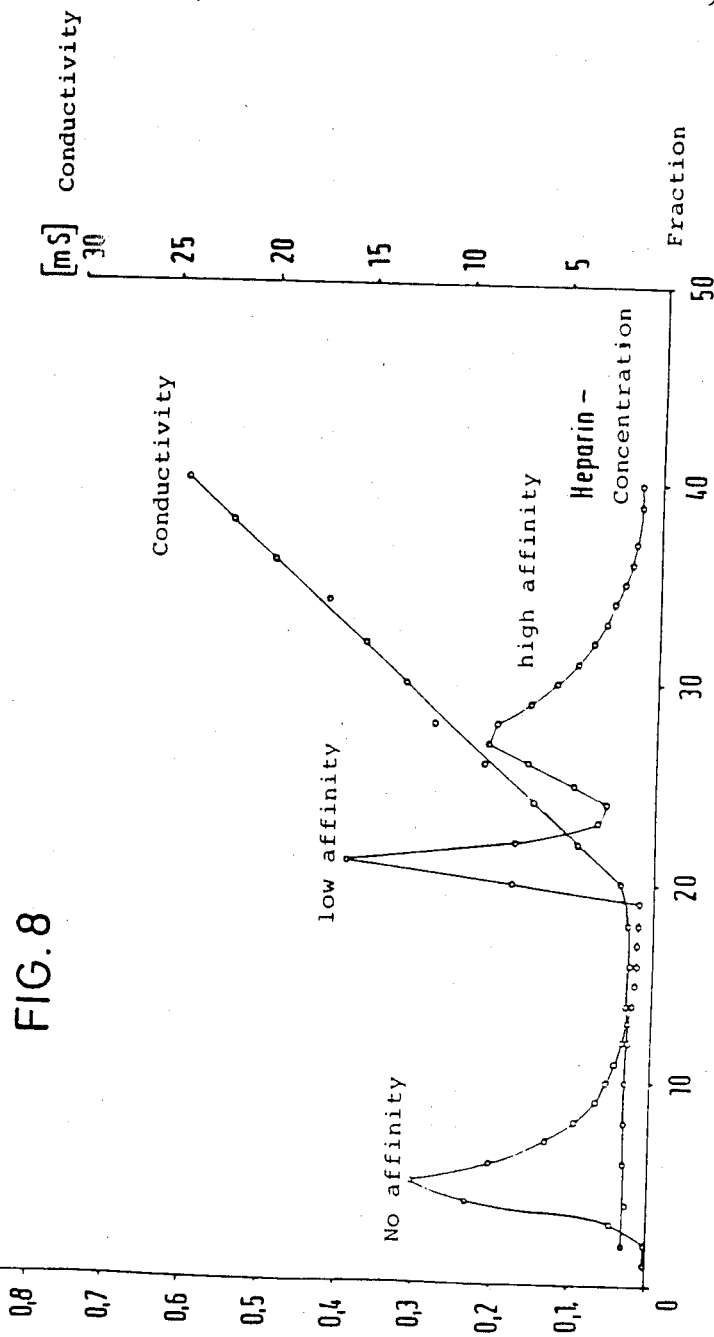
FIG. 8 illustrates the elution profile of the affinity chromatography of heparin used for the preparation of the heparin hydrolyzate according to the invention on antithrombin III coupled to Sepharose ®4B.

The product from Example 1 was tested with regard to its bonding chacteristics to antithrombin III in comparison with the starting heparin. Affinity chromatography over human antithrombin III, which was coupled to Sepharose ®4B by covalent boding, according to M. Hoock et al., FEBS Letters 66: 90, 1976, was performed. This produced three heparin fractions with different degrees of binding to antithrombin III (nonbinding, weakly binding and strongly binding fraction) for commercial heparin. The product from Example 1, in contrast, was bound not at all, or only as a weakly binding fraction, to antithrombin III. The elution profile of the affinity chromatography of the product according to the invention on antithrombin-III-Sepharose ® is recorded in FIG. 7, and that of the heparin used for the preparation in FIG. 8. Conditions of the affinity chromatography on antithrombin III, which was coupled to Sepharose ®4B were as follows:
Buffer 1: 0.05M Tris-buffer, 0.05M NaCl solution, pH 7.5
Buffer 2: 0.05M Tris-buffer, 2.5M NaCl solution; pH 7.5
Elution with (1) 20 ml buffer 1 (2) 30 ml buffer 1 and 30 ml buffer 2 (linear gradient)
Rate of flow: 15 ml/hr
Amount of sample: 1.0 ml; 3 mg/ml
Eluate samples of 2 ml were collected.

The sulfur content of the product of Example 1 decreased in comparison with the heparin used for the preparation from 11.5% to 9.8% (w/w).

The course of the acid hydrolysis was monitored with the aid of a heparin-sensitive coagulation test, the activated partial thromboplastin time. For this purpose, 0.8 ml samples were removed from the reaction mixture at defined times, neutralized with 5 mM sodium hydrogen carbonate solution in 0.9% NaCl solution and diluted to 100 ml with the same buffer. One part by volume of this stock solution was again diluted with four parts by volume 0.9% NaCl solution. A sample of 50 μl from this dilution was mixed with 950 μl human citrated plasma and the apTT was determined using the reagent Pathromtin ®, Behringwerke, Marburg.

The ball coagulometer KC 4 of Amelung GmbH, Lemgo, was used for the determination. Table 1 below shows the change, with time, in the measured coagulation time in seconds (means of four measurements) as well as the standard deviation and the coefficient of variation calculated from four measurements, respectively.

TABLE 1

| Coagulation activity of the heparin hydrolyzate (70° C.) | | | | | | | |
|---|---|---|---|---|---|---|---|
| Reagent blank | Coagulation time (sec.) after hydrolysis | | | | | | |
| (Not containing heparin) | 0 min | 15 min | 30 min | 50 min | 65 min | 80 min |
| Mean | 43.25 | 213.7 | 135.8 | 92.95 | 50.8 | 48.2 | 43.98 |
| S | 0.25 | 0.25 | 0.44 | 0.29 | 0.45 | 0.14 | 0.36 |
| VK (%) | 0.58 | 0.12 | 0.33 | 0.31 | 0.89 | 0.29 | 0.82 |

EXAMPLE 2

The product prepared according to Example 1 was tested for its ability to precipitate low-density lipoproteins (LDL) from human plasma. For this purpose, the product from Example 1 was dissolved in a concentration of 0.93 g/liter in 0.2M sodium acetate buffer that was adjusted to pH 4.85 with acetic acid. Then 500 μl human plasma was mixed with 500 μl of the acetate buffer containing the product from Example 1. After standing for ten minutes at room temperature, the mixture was filtered through a 0.4 μm filter or centrifuged, and the concentration of the supernatant cholesterol was determined. The LDL-cholesterol concentration precipitated by the herapin derivative was obtained by subtracting the value of the supernatant cholesterol from the total cholesterol content determined previously.

The precipitated LDL-cholesterol was plotted as the quotient of the precipitated LDL/analytical LDL on the ordinate in all subsequent graphs. The analytical LDL-cholesterol value was determined by the analytical LDL-test with herapin citrate (H. Wieland and D. Seidel, J. Lipid. Res. 24: 904, 1983). A quotient of 1 consequently represented the quantitative precipitation of the LDL-cholesterol.

Figure 9:
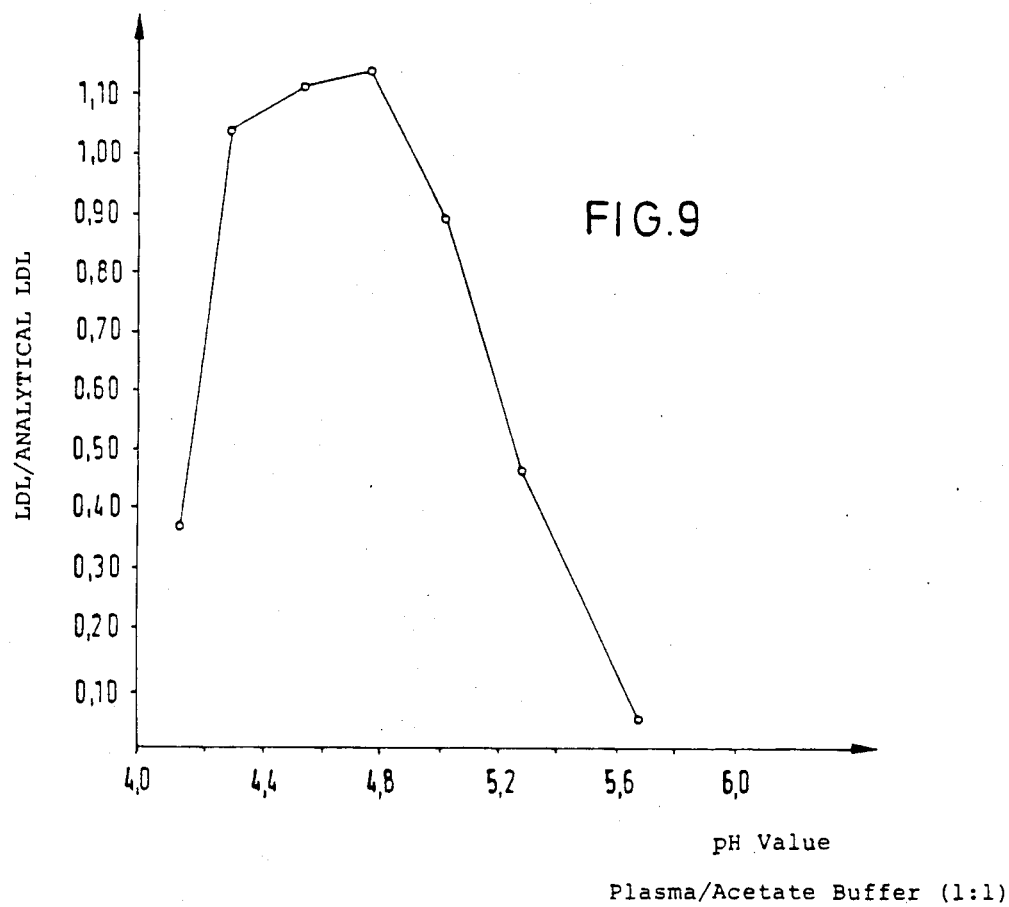
FIG. 9 shows the dependence on pH of the precipitation of a low density lipoprotein by the heparin hydrolyzate according to the invention.
Figure 10:
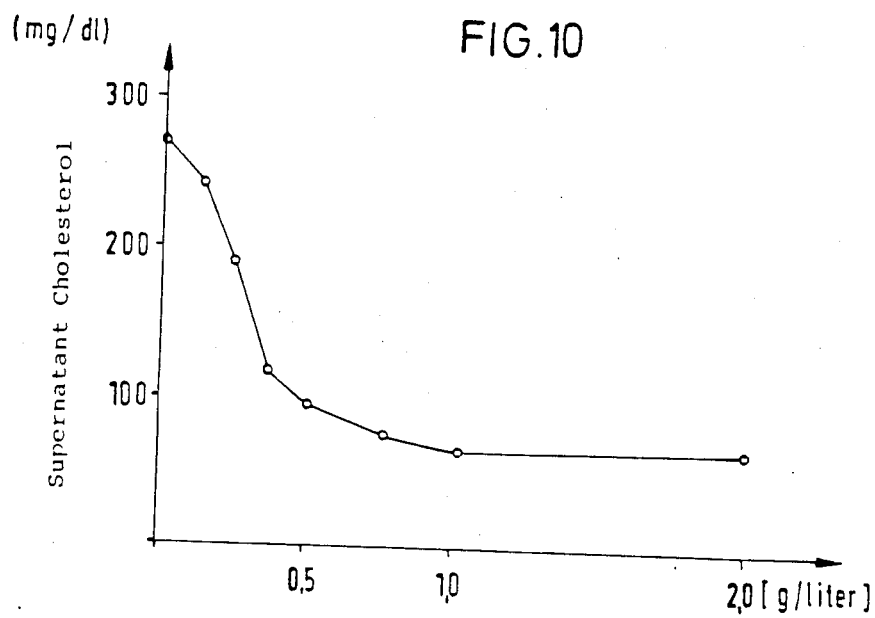
FIG. 10 shows the decrease of the supernatant cholesterol as a function of the amount of the heparin hydrolyzate according to the invention dissolved in a sodium acetate buffer at an acid pH.

The pH values were adjusted in the range from 4.0 to 5.4 by varying the amount of acetic acid required for the adjustment of the pH in the sodium acetate buffer. After mixing equal parts by volume of the human plasma with the solution of the herapin derivative (0.93 g/liter) in sodium acetate buffer, pH values were obtained that were plotted as the abscissa in graph form. FIG. 9 shows the pH dependence of the LDL-precipitation with the product from Example 1. FIG. 10 shows the decrease of the supernatant cholesterol as a function of the amount of product from Example 1 dissolved in the sodium acetate buffer, pH 4.85.

For comparison purposes, a test series was carried out to determine whether an LDL-precipitation can be demonstrated with the products of hydrolysis prepared according to the directions of German Offenlegensschrift DE-OS No. 31 23 806. A product was obtained that cannot be used as precipitating agent for the precipitation under the conditions described in Example 2 because of its coagulation activity of less than 0.1 IU/mg (USP XX). The content of free amine groups in this product was 550 μmol/g. The rate of the cleavage of this substance with heparinase is at 10.0% in comparison with heparin (=100%). The metachromatic dye effect with the dye toluidine blue, i.e. the dependence of the change in extinction at 623 nm on the concentration, which is triggered by the addition of the product prepared according to German Offenlegensschrift DE-OS No. 31 23 806 to the dye solution (10 mg/liter), is only 8% in comparison with heparin (=100%).

EXAMPLE 3

Analogous to the procedure described in Example 1, an identical hydrolysis test was performed with the difference being that the reaction temperature was at 50±0.5° C. Samples were also removed from the reaction mixture and their coagulation activity was determined, as in Example 1, with the aid of the apTT. Table 2 below contains a summary of the results of these coagulation tests.

The isolated product showed a coagulation activity of 4.5 IU/Mg. The ability to precipitate LDL is demonstrated in a precipitating experiment according to Example 2.

TABLE 2

| | Coagulation activity of the heparin hydrolyzate (50° C.) | | | | | | | | | | | |
|---|---|---|---|---|---|---|---|---|---|---|---|---|
| Reagent blank (not containing heparin) | Coagulation time (sec.) after hydrolysis | | | | | | | | | | | |
| | 0 h | 1 h | 2 h | 3 h | 4 h | 5 h | 6 h | 7 h | 8 h | 10 h | 12 h |
| Mean | 46.23 | 212.6 | 168.9 | 139.9 | 118.2 | 97.20 | 87.40 | 73.7 | 67.65 | 64.53 | 59.21 | 52.1 |
| S | 0.46 | 0.99 | 0.50 | 0.72 | 0.51 | 0.26 | 0.46 | 0.31 | 0.45 | 0.37 | 0.48 | 0.6 |
| $V_K$ (%) | 0.99 | 0.45 | 0.29 | 0.52 | 0.43 | 0.27 | 0.53 | 0.42 | 0.67 | 0.57 | 0.81 | 1.2 |

EXAMPLE 4

A heparin hydrolyzate prepared according to the directions in Example 1, with a coagulation activity of 1.75 IU/mg, was dissolved in a concentration of 62.5 mg/ml in H$_2$O, filled in 5 ml ampules and sterilized with heat for 40 minutes at 110° C. The coagulation activity found in this solution was 107 IU/ml (USP XX). This solution was then tested in vivo for its coagulation activity after intravenous administration in increasing doses in rabbits as experimental animals. Dose, weight of the experimental animals, as well as the amounts of heparin hydrolyzate injected into the animals can be found in the following Table 3. One animal was used for each dosage group.

TABLE 3

Experimental parameters in Example 4.

| No. | Animal | Weight (kg) | Dose (ml) | mg Heparin derivative/kg |
|---|---|---|---|---|
| 1 | K-II | 3.79 | 1.26 | 20.78 |
| 1 | K-IV | 4.5 | 0.75 | 10.42 |
| 3 | K-III | 4.3 | 0.36 | 5.23 |
| 4 | K-V | 5.2 | 0.22 | 2.64 |
| 5 | K-I | 5.64 | 0.12 | 1.33 |

The results of some coagulation parameters relevant to coagulation can be found in Tables 4 to 8.

The overall result was that in comparison with natural heparin, a very high load of heparin derivative (20.8 mg/kg body weight) was tolerated without any lasting influence on the coagulation system. Bleeding problems did not occur in any of the experimental animals.

TABLE 4

Parameters relevant to coagulation in the in vivo test (Ex. 4), performed employing Animal K-II, weighing 3.79 kg and a dose of 1.26 ml. of heparin derivative

| Time | Thrombin time sec | Fibrinogen mg/dl | PTT sec. | Thrombocytes $10^3/\mu l$ | Heparin IU/ml with S2222 acc. Teien etal. |
|---|---|---|---|---|---|
| 0 | 16.1 | 240 | 45.3 | 208 | 0 |
| 15 | >300 | 210 | 44.9 | — | <10.1 |
| 30 | >300 | 250 | 72.5 | 275 | 0.19 |
| 60 | >300 | 230 | 62.3 | 284 | 0.11 |
| 120 | 43.1 | 150 | 50.8 | — | <10.1 |
| 240 | 22.4 | 200 | 24.1 | 240 | <10.1 |

TABLE 5

Parameters relevant to coagulation in the in vivo test (Ex. 4), performed employing Animal K-IV, weighing 4.5 kg, and administering a dose of .75 ml of heparin derivative.

| Time | Thrombin time sec | Fibrinogen mg/dl | PTT sec. | Thrombocytes $10^3/\mu l$ | Heparin IU/ml with S2222 acc. Teien etal. |
|---|---|---|---|---|---|
| 0 | 15.3 | 190 | 21.1 | 219 | 0 |
| 15 | 65.0 | 200 | 27.0 | 241 | <0.1 |
| 30 | 29.1 | 190 | 24.9 | 236 | <0.1 |
| 60 | 20.0 | 190 | 22.6 | 235 | <0.1 |
| 120 | 16.0 | 190 | 22.3 | 211 | <0.1 |
| 240 | 15.7/14.6 | 170/180 | 23.3/25.2 | 247/224 | — |

TABLE 6

Parameters relevant to coagulation in the in vivo test (Ex. 4), performed employing Animal K-III, weighing 4.3 kg and administering a dose of 0.36 ml of heparin derivative.

| Time | Thrombin time sec | Fibrinogen mg/dl | PTT sec. | Thrombocytes $10^3/\mu l$ | Heparin IU/ml with S2222 acc. Teien etal. |
|---|---|---|---|---|---|
| 0 | 16.4 | 140 | 62 | — | 0 |
| 15 | 54.0 | 150 | 30.2 | 191 | <0.1 |
| 30 | 24.3 | 150 | 27.2 | 220 | <0.1 |
| 60 | 18.8 | 140 | 26.1 | 307 | <0.1 |
| 120 | — | — | — | — | — |
| 240 | — | — | — | — | — |

TABLE 7

Parameters relevant to coagulation in the in vivo test (Ex. 4), performed employing Animal K-V, weighing 5.2 kg and administering a dose of 0.22 ml of heparin derivative.

| Time | Thrombin time sec | Fibrinogen mg/dl | PTT sec. | Thrombocytes $10^3/\mu l$ | Heparin IU/ml acc. Teien etal. |
|---|---|---|---|---|---|
| 0 | 16.9 | 200 | 21.0 | 241 | 0 |
| 15 | 34.3 | 200 | 24.0 | 288 | <0.1 |
| 30 | 21.6 | 190 | 20.9 | 289 | <0.1 |
| 60 | 18.2 | 200 | 22.1 | 259 | <0.1 |
| 120 | 16.8 | 190 | 22.4 | 261 | <0.1 |
| 240 | 17.1 | 150 | 20.5 | 283 | <0.1 |

TABLE 8

Parameters relevant to coagulation in the in vivo test (Ex. 4), performed employing Animal K-I, weighing 5.64 kg and administering a dose of 0.12 ml of heparin derivative.

| Time | Thrombin time sec | Fibrinogen mg/dl | PTT sec. | Thrombocytes $10^3/\mu l$ | Heparin IU/ml acc. Teien etal. |
|---|---|---|---|---|---|
| 0 | 15.6 | 280 | 40.0 | (126) | 0 |
| 15 | 19.3 | 280 | 41.0 | — | <0.1 |
| 30 | 16.0 | 180 | 34.5 | 194 | <0.1 |
| 60 | 15.9 | 180 | 33.0 | (124) | <0.1 |
| 120 | 18.6 | 180 | 25.7 | — | <0.1 |
| 240 | 15.2 | 210 | 20.7 | 240 | <0.1 |

EXAMPLE 5

A heparin hydrolyzate was prepared according to the directions given in Example 1 and was reacted with acetic anhydride in a subsequent step. The objective of this step was the acetylation of the amine group released in the hydrolysis step by a known method.

For this purpose, 2.5 g of a heparin hydrolyzate (prepared according to Example 1) with a coagulation activity of 5.71 IU/mg (USP XX) was dissolved in 279 ml $H_2O$, and 30 ml methanol as well as 1.5 g sodium carbonate were added. While cooling this solution with ice, 6 ml acetic anhydride was added dropwise over a period of 30 minutes. The pH was maintained between 7.0 and 7.5 with 3M $Na_2CO_3$ solution. The reaction mixture was subsequently agitated for 2 hours in the ice bath and then dialyzed against water for 2 days. The obtained product was precipitated by known methods with ethanol and dried overnight in the vacuum drying cabinet at 60° C.. The white, slightly hygroscopic product (yield: 2.1 g) had a coagulation activity of 16.9 IU/mg (USP XX).

Figure 11:
FIG. 11 shows the 400-MHz $^1$H-NMR spectrum of the acylated heparin hydrolyzate according to the invention demonstrating an elevated peak of the N-acetyl signal.

The 400-MHz $^1$H-NMR spectrum of the product is shown in FIG. 11. The spectrum (50 mg/ml $D_2O$; internal standard: HDO; rel. to TMS: $\delta=4.8$ ppm) has, in comparison to heparin or the products obtained according to Examples 1 and 2, an elevated peak of the N-acetyl signal, which was expected. The product contained, as is apparent from the spectrum, some ethanol as a contaminant (1.18, 3.59 ppm). The content of free amine groups decreased from 145 $\mu$mol/g in the starting material to 4.4 $\mu$mol/g. The rate of cleavage with heparinase changed from 53% (heparin=100%) of the starting material to 45% in the acetylated product. The specific rotation changes from $(\delta)_D^{20}=+51°$ to $+44.5°$. The metachromatic dye effect, measured with toluidine blue, changes in comparison with heparin (=100%) from 85% in the starting material to 82%.

Figure 12:
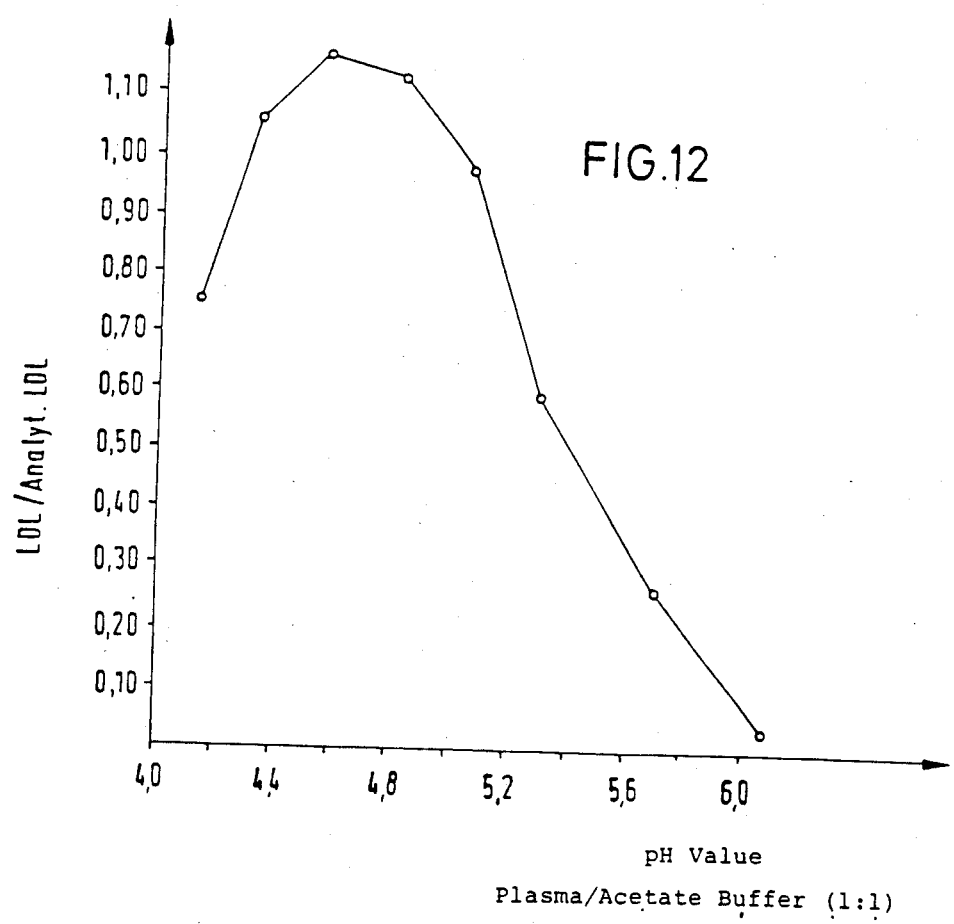
FIG. 12 demonstrates the dependence on the pH of the LDL precipitation employing the acylated heparin hydrolyzate according to the invention.

The ability of the product to precipitate LDL from human plasma was tested in an additional experiment. The pH-dependence of the LDL precipitation, which was performed as described in Example 2, can be found in FIG. 12.

EXAMPLE 6

A heparin hydrolyzate prepared according to the directions in Example 1 was reacted with succinic anhydride in a subsequent step. The objective of this step was the succinylation, by known methods, of the amine groups released by the hydrolysis step. For this purpose, 2 g of a heparin hydrolyzate (according to Example 1) with a coagulation activity of 5.71 IU/ml (USP XX) was dissolved in 24 ml H$_2$O and reacted in portions, at room temperature, with 600 mg succinic anhydride. The pH was maintained at 8.0 with 5N NaOH. After the completion of the addition, the solution was adjusted to pH 7.5 and dialyzed for two days against water. The product was precipitated with ethanol and the separated precipitate was dried overnight at 60° C. in the vacuum drying cabinet. The white product had a coagulation activity of 18.8 IU/mg (US XX).

Figure 13:
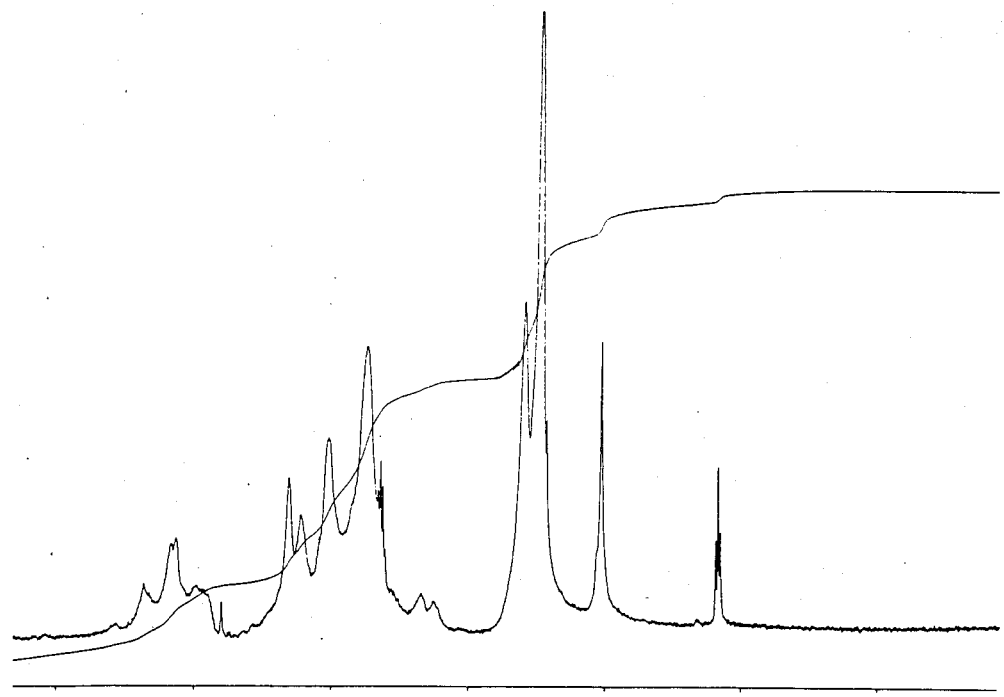
FIG. 13 shows the 400 MHz $^1$H-NMR spectrum of succinylated heparin hydrolyzate prepared according to the process of the invention.

The 400-MHz $^1$H-NMR spectrum of the product is found in FIG. 13 (50 mg /ml$^{-1}$ D$_2$O; internal standard: HDO;$\delta$=4.8 ppm rel. TMS). Several of the characteristics of the product are compared with those of the starting material and heparin in Table 9 below. The pH-dependence of the LDL-precipitation produced the curve in FIG. 14. The precipitation was performed under the conditions stated in Example 2.

TABLE 9

Characteristics of the N—succinylated hydrolyzate in comparison with natural heparin and nonsuccinylated heparin hydrolyzate

|  | Heparin | Heparin hydrolyzate | Succinylated product |
|---|---|---|---|
| Free amine groups (umol/g) | 17.4 | 145 | 5.1 |
| Rate of heparinase cleavage | 100% | 53% | 48% |
| Specific rotation $(\alpha)_D^{20}$ | 52.5° | +51° | +30.8° |
| Metachromatic effect (toluidine blue) | 1.00 | 0.85 | 0.73% |

While there have been described what are presently believed to be preferred embodiments of the invention, it will be apparent to a person skilled in the art that numerous changes can be made in the ingredients, conditions and proportions set forth in the foregoing embodiments without departing from the invention as described herein and as defined in the appended claims.

We claim:

1. A heparin derivative compound characterized by a substantially selective low density lipoprotein precipitating action that lowers the low density lipoprotein content in blood without a significant anticoagulent effect.

2. The heparin derivative compound according to claim 1 which is selected from the group consisting of hydrolyzed heparin and hydrolyzed heparin acylated at free amine groups.

3. The heparin derivative compound according to claim 1, characterized by a coagulation activity of less than about 20 IU/mg and low binding affinity to anti-thrombin III as compared to heparin.

4. The heparin derivative according to claim 2, wherein the hydrolyzed heparin has a content of free amine groups of 50 to 400 $\mu$mol/g and the hydrolyzed heparin acylated at free amine groups has a content of free amine groups of 2 to 10 $\mu$mol/g.

5. A heprin derivative compound selected from the group consisting of hydrolyzed heparin and acylated hydrolyzed heparin which is characterized by its low density lipoprotein precipitating action at an acid pH that lowers the low density lipoprotein content in blood without a significant anticoagulent effect; said heparin derivative compound is further characterized by a coagulation activity of about 20 IU/mg or less and low binding affinity to antithrombin III as compared to heparin.

6. The heparin derivative compound according to claim 5 wherein said acylated hydrolyzed heparin is prepared by reacting a heparin hydrolyzate with anhydrides or acid halides selected from the group consisting of oxalic acid, malonic acid, succinic acid, haloacetic acid, halopropionic acid, haloacylic acid and substituted phthalic acid.

7. A process for the preparation of low density lipoprotein-precipitating heparin derivatives from heparin which comprises the steps of:
   (a) subjecting heparin and any desired salts thereof to a mild, controlled, acid hydrolysis reaction at a predetermined acid pH for a period of time of less than about 90 minutes at a temperature of less than about 70° C.;
   (b) cooling the reaction and adjusting the pH to a level higher than the predetermined acid pH of step (a) by the addition of an alkali to create a reaction product;
   (c) dialyzing the reaction;
   (d) drying the reaction product by known methods;
   said reaction product comprising a heparin derivative capable of precipitating low density lipoproteins without a significant anticoagulent effect.

8. The process according to claim 7 which further comprises acylating the reaction product at free amine groups thereof to form a hydrolyzed, acylated heparin derivative capable of precipitating low density lipoproteins without a significant anticoagulent effect.

9. The process according to any one of claims 7 or 8 wherein said predetermined pH is between about 1.0 and 5.0, said acid hydrolysis is performed with aqueous 0.2 to 0.33M acid at 45° to 70° C., said cooling is conducted between 0° C. and 30° C. and in step (b), the pH is adjusted to between 6.0 and 8.0.

10. The process according to claim 9, wherein said acid is a mineral acid.

11. The process according to claim 7, wherein an acid buffer is added during the acid hydrolysis treatment reaction of step (a).

12. The process according to claim 7, wherein the hydrolysis treatment is carried out a pH of 1.0, a temperature of 70° C. and for a period of 80 minutes.

13. The process according to claim 7, wherein said alkali is an aqueous alkali hydroxide solution.

14. The process according to claim 8, wherein the reaction product is acylated at free amine groups by reaction with mono-or dicarboxylic acids of 1 to 8 carbon atoms or their anhydrides, acid halides or derivatives substituted with halogens at the hydrocarbon portion thereof.

15. A pharmaceutical preparation for the treatment of hyperlipidemia and the prevention of angionesis of tumors comprising a heparin derivative compound selected from the group consisting of hydrolyzed heparin and hydrolyzed heparin acylated at free amine groups, said heparin derivative characterized by its low density lipoprotein precipitating action that lowers the low density lipoprotein content in blood without a significant anticoagulent effect.

16. The pharmaceutical preparation according to claim 15 wherein the heparin derivative is characterized by a coagulation activity of less than about 20 IU/mg and low binding affinity to antithrombin III as comapred to heparin.

17. The pharmaceutical preparation according to claim 15 wherein the hydrolyzed heparin has a content of free amine groups of 50 to 400 μmol/g and the hydrolyzed heparin acylated at free amine groups has a content of free amine groups of 2 to 10 μmol/g.

18. A method of treatment for hyperlipidemia which comprises administering to a volume of blood, plasma or solutions thereof a therapeutically effective amount of a heparin derivative compound selected from the group consisting of hydrolyzed heparin and hydrolyzed heparin acylated at free amine groups, said heparin derivative compound characterized by its low density lipoprotein precipitating action that lowers the low density lipoprotein content in blood without a significant anticoagulent effect.

19. A method of treatment for the prevention of angionesis of tumors which comprises administering to a volume of blood, plasma or solutions thereof a therapeutically effective amount of a heparin derivative selected from the group consisting of hydrolyzed heparin ad hydrolyzed heparin acylated at free amine groups.

20. The method of treatment according to any one of claims 18 and 19 wherein the heparin derivative is characterized by a coagulation activity of less than 20 IU/mg and low binding affinity to antithrombin III as compared to heparin.

21. The method of treatment according to anyone of claims 18 and 19 wherein the hydrolyzed heparin has a content of free amine groups of 50 to 400 μmol/g and the hydrolyzed heparin acylated at free amine groups has a content of free amine groups of 2 to 10 μmol/g.

* * * * *